United States Patent
Hennard et al.

(10) Patent No.: US 9,918,752 B2
(45) Date of Patent: Mar. 20, 2018

(54) SPINAL IMPLANT SYSTEM AND METHOD

(71) Applicant: Warsaw Orthopedic, Inc., Warsaw, IN (US)

(72) Inventors: Michelle M. Hennard, Memphis, TN (US); Mark R. Grizzard, Munford, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/689,312

(22) Filed: Nov. 29, 2012

(65) Prior Publication Data
US 2014/0148865 A1    May 29, 2014

(51) Int. Cl.
A61B 17/70    (2006.01)

(52) U.S. Cl.
CPC ................................ *A61B 17/7086* (2013.01)

(58) Field of Classification Search
CPC ............. A61B 17/70; A61B 17/7074–17/7088
See application file for complete search history.

(56) References Cited

U.S. PATENT DOCUMENTS

| | | | |
|---|---|---|---|
| 5,020,519 A * | 6/1991 | Hayes et al. .................. 606/237 |
| 6,770,074 B2 | 8/2004 | Michelson | |
| 7,166,107 B2 | 1/2007 | Anderson | |
| 7,188,626 B2 | 3/2007 | Foley et al. | |
| 7,465,306 B2 * | 12/2008 | Pond et al. .................. 606/86 A |
| 7,666,189 B2 * | 2/2010 | Gerber ............... A61B 17/7074 606/104 |
| 7,931,677 B2 * | 4/2011 | Abdelgany .................... 606/279 |
| 8,192,438 B2 * | 6/2012 | Garamszegi ................ 606/86 A |
| 8,273,089 B2 * | 9/2012 | Jackson ....................... 606/86 A |
| 8,308,774 B2 * | 11/2012 | Hoffman et al. .............. 606/279 |
| 8,556,904 B2 * | 10/2013 | Rezach et al. .............. 606/86 A |
| 8,608,746 B2 * | 12/2013 | Kolb et al. .................. 606/86 A |
| 8,685,029 B2 * | 4/2014 | Dziedzic et al. ........... 606/86 A |
| 2004/0049191 A1 * | 3/2004 | Markworth et al. ............ 606/61 |
| 2004/0147937 A1 * | 7/2004 | Dunbar, Jr. ........ A61B 17/7091 606/99 |
| 2006/0074418 A1 * | 4/2006 | Jackson .......................... 606/61 |
| 2007/0032162 A1 * | 2/2007 | Jackson ........................... 446/1 |

(Continued)

OTHER PUBLICATIONS

Notice of Reasons of Rejection issued by the Japan Patent Office dated Sep. 12, 2017 of Japanese patent application No. 2015-545098 filed May 29, 2015 and translated document.

*Primary Examiner* — Jan Christopher Merene
*Assistant Examiner* — Steven Cotroneo

(57) ABSTRACT

A spinal implant system comprises a first instrument extending between a first end including an outer surface and a second end configured for engaging a first implant. The first instrument defines a passageway. A second instrument is configured for disposal within the passageway, and extending between a first end including an inner surface and a second end configured for engaging a second implant. The inner surface is engageable with the outer surface to fix the second instrument in a selected orientation relative to the first instrument. The second end of the first instrument is disposable between an expanded orientation and a non expanded orientation to engage the first implant and the second end of the second instrument is translatable relative to the first end of the second instrument to dispose the second implant with the first implant. Methods of use are disclosed.

18 Claims, 16 Drawing Sheets

(56) References Cited

U.S. PATENT DOCUMENTS

| | | | |
|---|---|---|---|
| 2007/0093849 A1* | 4/2007 | Jones et al. | 606/99 |
| 2007/0213714 A1 | 9/2007 | Justis | |
| 2007/0213722 A1* | 9/2007 | Jones et al. | 606/61 |
| 2008/0228228 A1* | 9/2008 | Hestad et al. | 606/246 |
| 2008/0243190 A1* | 10/2008 | Dziedzic et al. | 606/278 |
| 2010/0292742 A1* | 11/2010 | Stad | A61B 17/7091 606/86 A |
| 2011/0218581 A1* | 9/2011 | Justis | A61B 17/708 606/86 A |
| 2012/0271365 A1* | 10/2012 | Daubs et al. | 606/86 A |
| 2014/0148865 A1* | 5/2014 | Hennard et al. | 606/86 A |

\* cited by examiner

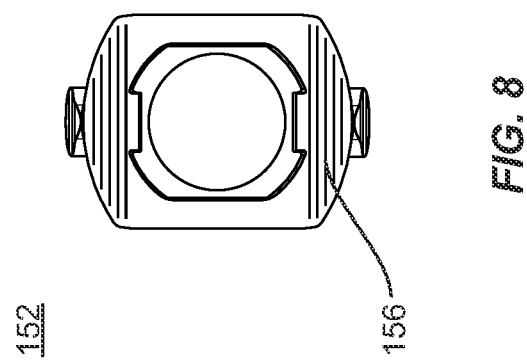
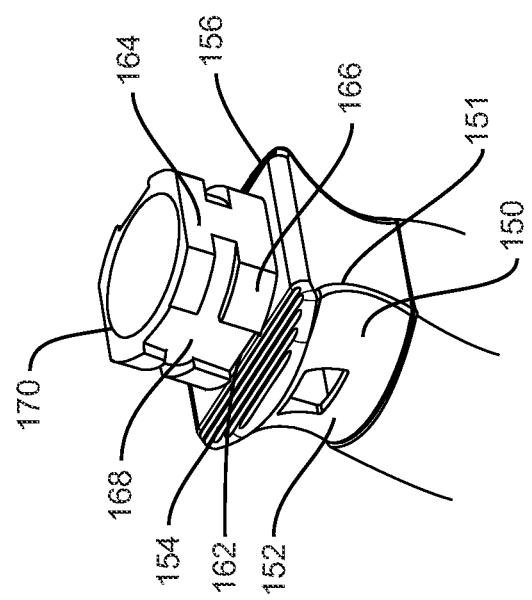

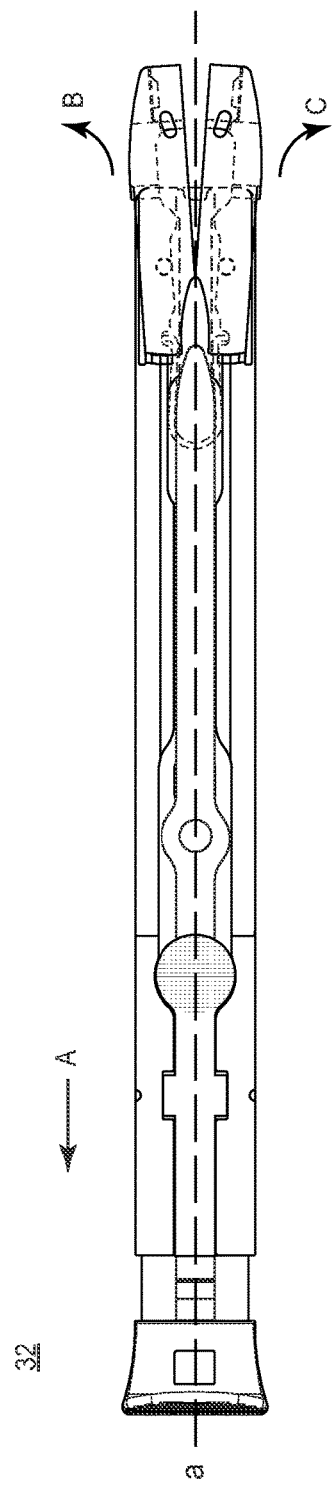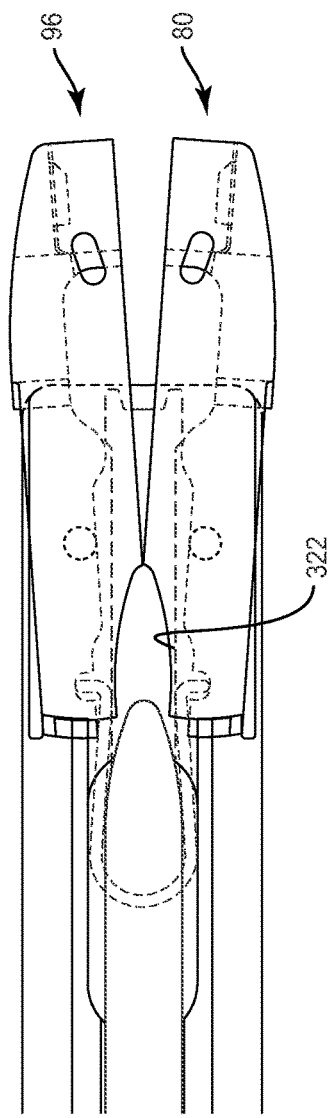
FIG. 16
FIG. 17

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a spinal implant system is provided. The spinal implant system comprises a first instrument extending between a first end including an outer surface and a second end configured for engaging a first implant. The first instrument defines a passageway. A second instrument is configured for disposal within the passageway, and extends between a first end including an inner surface and a second end configured for engaging a second implant. The inner surface is engageable with the outer surface to fix the second instrument in a selected orientation relative to the first instrument. The second end of the first instrument is disposable between an expanded orientation and a non expanded orientation to engage the first implant and the second end of the second instrument is translatable relative to the first end of the second instrument to dispose the second implant with the first implant.

BRIEF DESCRIPTION OF THE DRAWINGS

The present disclosure will become more readily apparent from the specific description accompanied by the following drawings, in which:

FIG. 7 is an enlarged break away view of the components shown in FIG. 1;

FIG. 8 is an enlarged top view of the components shown in FIG. 1;

FIG. 16 is a side view of the components shown in FIG. 14;

FIG. 17 is an enlarged break away view of the components shown in FIG. 16;

Like reference numerals indicate similar parts throughout the figures.

DETAILED DESCRIPTION

Figure 1:
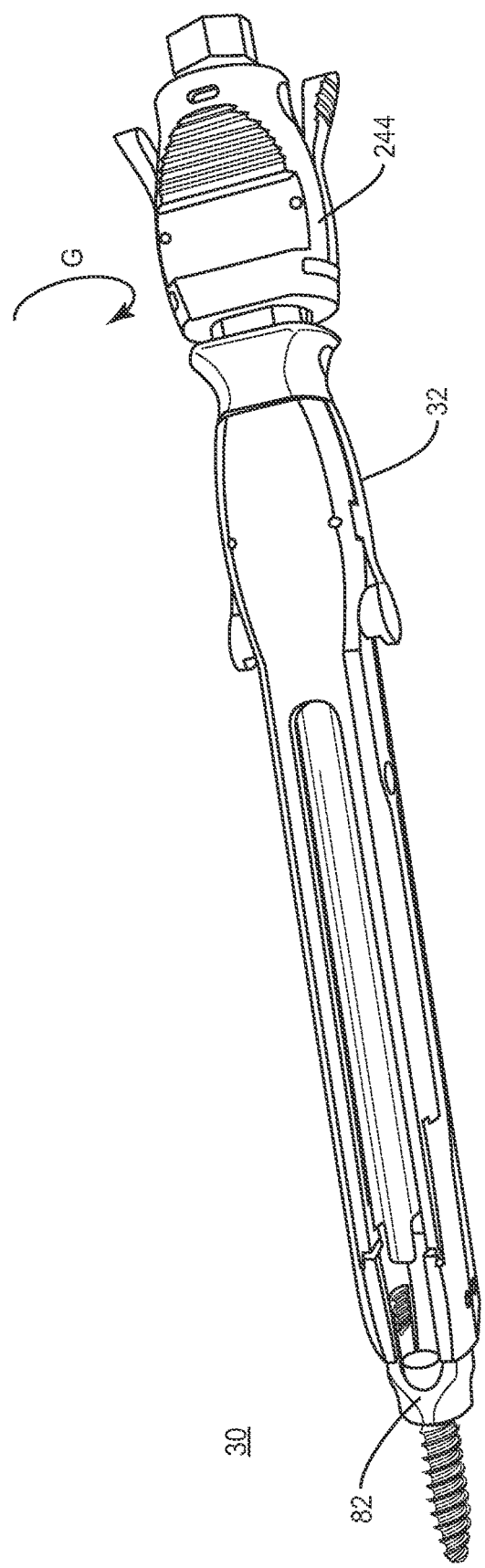
FIG. 1 is a perspective view of components of one embodiment of a system in accordance with the principles of the present disclosure.
Figure 2:
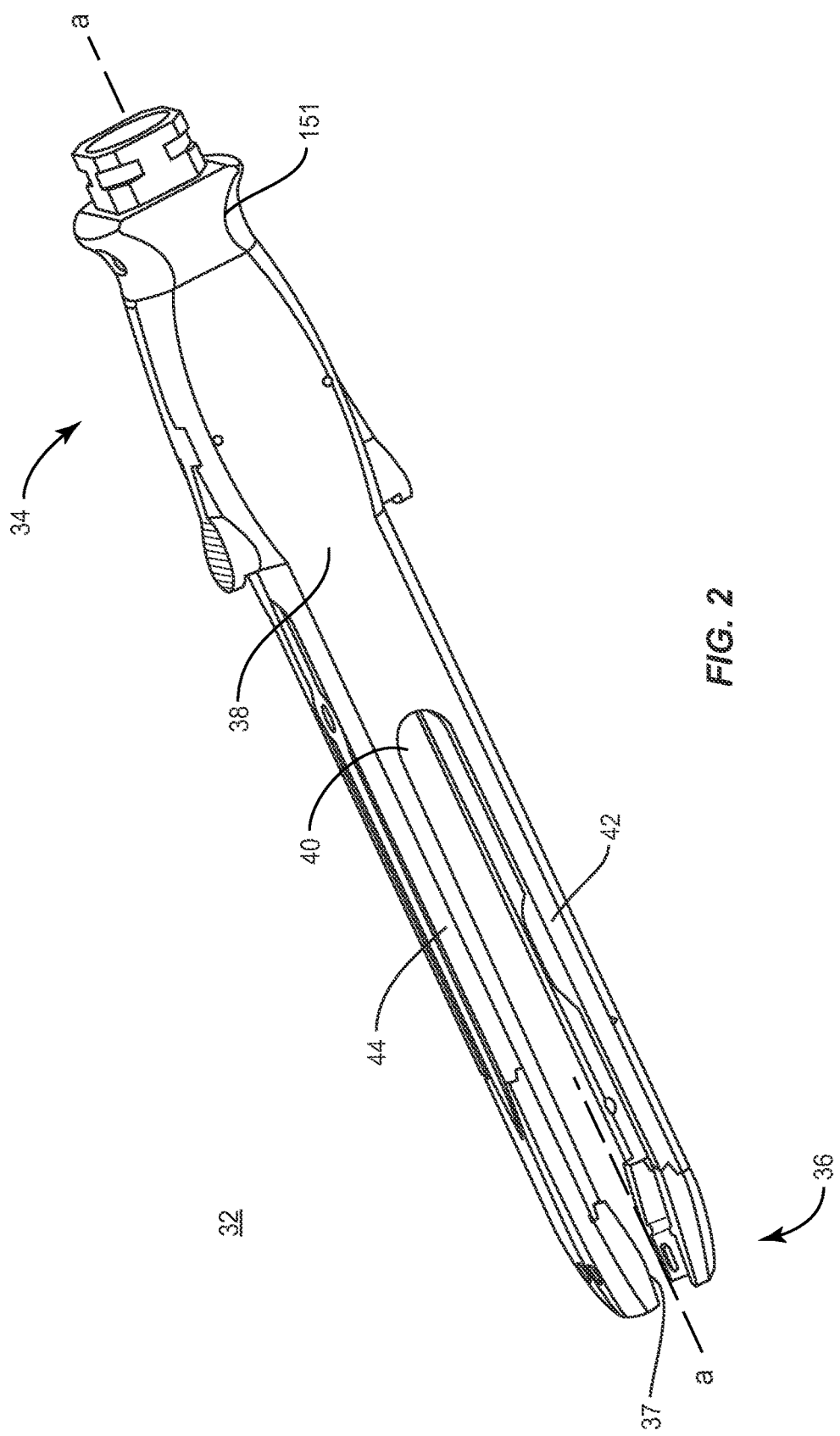
FIG. 2 is a perspective view of components of the system shown in FIG. 1.
Figure 3:
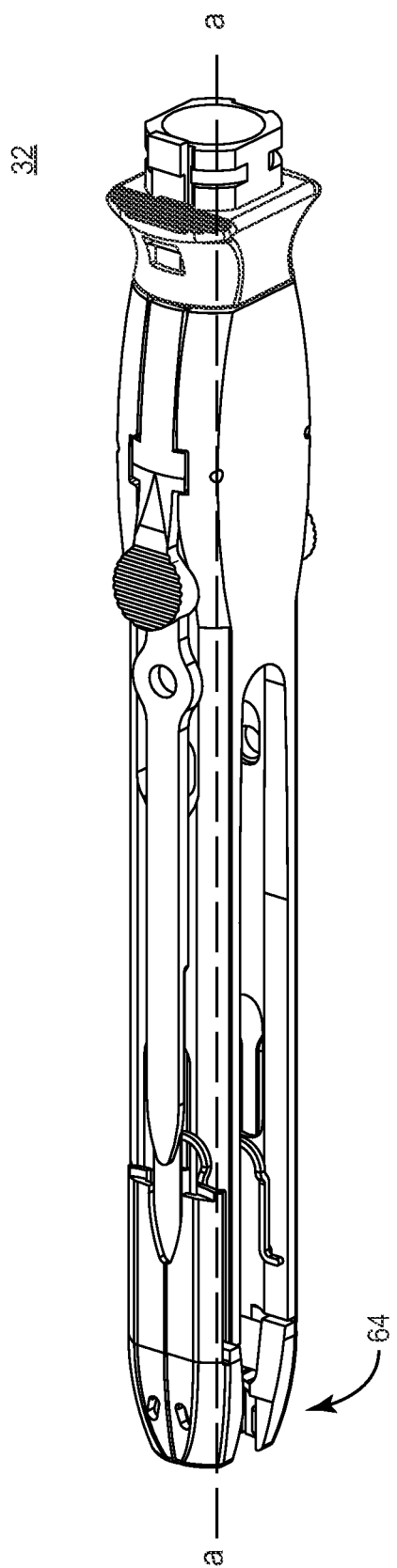
FIG. 3 is a perspective view of components of the system shown in FIG. 1.
Figure 4:
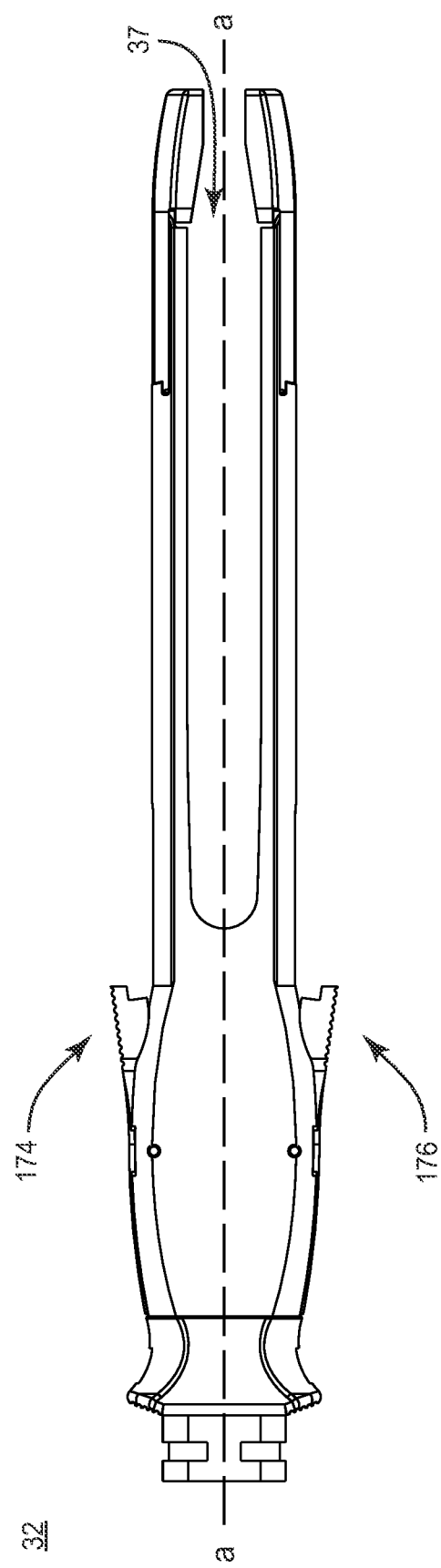
FIG. 4 is a side view of components of the system shown in FIG. 1.
Figure 5:
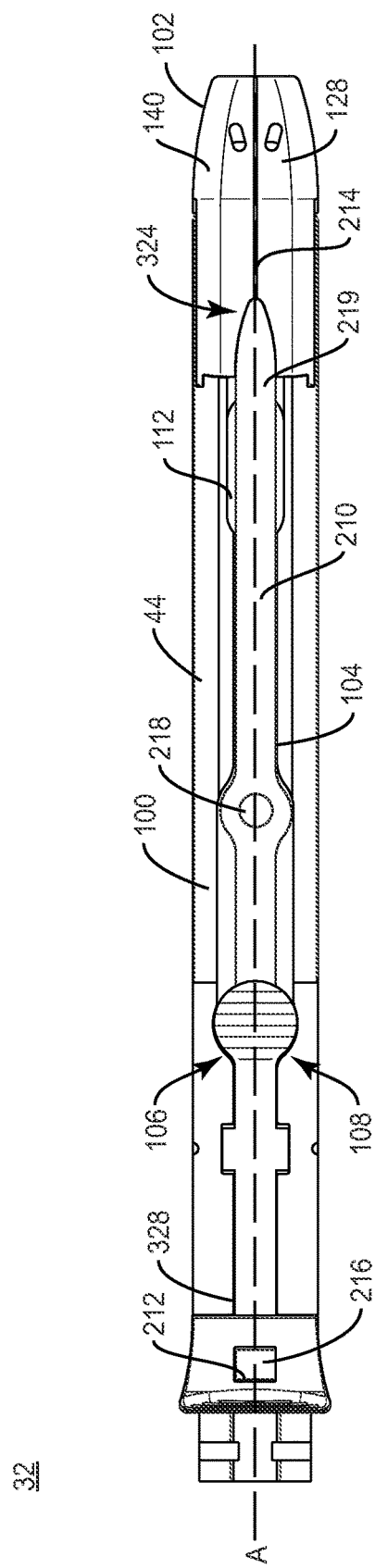
FIG. 5 is a side view of components of the system shown in FIG. 1.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the surgical implant system includes a bone fastener that allows the head to be captured and retained under tension and compression. It is envisioned that compression may be applied in a cephalad/caudal direction or a lateral direction. It is further envisioned that the tension may be applied through a member, such as, for example, an extender and that compression may be applied through another member, such as, for example, a reducer.

It is envisioned that the system may include instruments that are connected or attached to an extender(s) such as, for example, a lateral translation handle or derotaton instruments. It is further envisioned that the system may have an extender with a quick release mechanism to allow the extender to slide into engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In one embodiment, a system is provided that includes an instrument, such as, for example, a minimally invasive deformity extender. In one embodiment, the extender includes a cap. In one embodiment, the extender includes a uniform body, which defines a smooth cap. In one embodiment, the extender includes grooves that engage with the cap to facilitate movement of the cap during connection/engagement with an implant. In one embodiment, the extender defines an indicator window. The window includes depth markings such that a practitioner may gauge reduction positioning and determine when an implant has been fully reduced into a surgical site. In one embodiment, the reduction window is 101 millimeters (mm) long.

In one embodiment, a system is provided that includes an extender and a reducer. The extender and reducer are rotated 90 degrees to facilitate disposal of the components in a selected orientation and a mating engagement therebetween, for example, a stacking of the components, for example, when used in expansive surgical deformity cases. The stacking allows release from an implant. In one embodiment, the instrument is configured such that the instrument can only be moved into a selected orientation for reducing an implant. In one embodiment, the extender includes at least two buttons that resist and/or prevent undesired, for example, accidental or inadvertent disengagement of the instrument from an implant when force is applied to the buttons.

In one embodiment, an instrument is provided that includes an extender and a sequential reducer. The reducer and a top of the extender are aligned such that the reducer can fully set a rod into a surgical site. In one embodiment, the extender is rotated for multiple vertebral level placement. For example, when the extender and reducer are rotated 180 degrees, the surfaces of the extender and reducer are selectively aligned to fully set the rod. In one embodiment, a stop is provided. When the reducer and the top of the extender are disposed out of alignment and in a non mating relative orientation, the rod will not fully set into the implant, such as, for example, a screw. The stop prevents the practitioner from rotating the instrument 90 degrees and prevents misalignment of instrument parts. In one embodiment, the extender includes an implant engagement end. In one embodiment, the implant engagement end is 19 mm wide.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-17, there is illustrated components of a surgical system, such as, for example, a spinal implant system 30 in accordance with the principles of the present disclosure.

The components of spinal implant system 30 can be fabricated from biologically acceptable materials suitable for medical applications, including metals, synthetic polymers, ceramics and bone material and/or their composites, depending on the particular application and/or preference of a medical practitioner. For example, the components of spinal implant system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 30 may have material composites, including the above materials, to achieve various desired characteristics such as strength, rigidity, elasticity, compliance, biomechanical performance, durability and radiolucency or imaging preference. The components of spinal implant system 30, individually or collectively, may also be fabricated from a heterogeneous material such as a combination of two or more of the above-described materials. The components of spinal implant system 30 may be monolithically formed, integrally connected or include fastening elements and/or instruments, as described herein.

Spinal implant system 30 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that spinal implant system 30 and related methods may be employed with treatments that reduce a spinal rod with the bone fastener using minimally invasive and percutaneous techniques.

Spinal implant system 30 includes a first instrument, such as, for example, an extender 32. Extender 32 is configured for releasable engagement with a second instrument, such as, for example, a reducer to facilitate disposal and reduction of implants, such as, for example, a screw and a rod, within a surgical site. Extender 32 extends between a first end 34 and a second end 36. Extender 32 defines a first longitudinal axis a and includes a passageway 37 configured for engagement with the second instrument. It is contemplated that the cross-section of extender 32 may have various configurations, for example, round, cylindrical, partially cylindrical, oval, rectangular, polygonal, irregular, tapered, offset, staggered, uniform and non-uniform. It is further envisioned that one or all of the surfaces of extender 32 may have alternate surface configurations, such as, for example, rough, threaded for connection with surgical instruments, arcuate, undulating, porous, semi-porous, dimpled, polished and/or textured according to the requirements of a particular application.

End 34 includes an outer surface 38. Surface 38 defines a wall 40 that has a cylindrical cross-section configuration. It is contemplated that wall 40 may be variously configured according to the requirements of a particular application. Wall 40 defines two spaced apart arms, such as, for example, a first arm 42 and a second arm 44. Arm 42 extends between a proximal portion 46 and a distal portion 48. Arm 42 includes a wall that defines a channel 50 that extends between portions 46, 48. Channel 50 is configured for engagement with a portion of a locking member as described below. It is contemplated that channel 50 may have various configurations, such as, for example, cylindrical, partially cylindrical, rectangular, polygonal, irregular, tapered, offset, staggered, uniform and non-uniform.

Portion 46 includes two spaced apart openings 52, 54 configured for engagement with components of a locking member, such as, for example, biasing members. A window 56 is defined within channel 50 and is configured to align with a second window 110 to indicate axial translation of a second instrument disposed within extender 32, as described herein. It is contemplated that window 56 may be variously configured such as, for example, round, cylindrical, partially cylindrical, oval, rectangular, polygonal, irregular, tapered, offset.

Portion 48 includes an opening 58 configured for disposal of components of a locking member, such as, for example, a biasing member. Opening 58 may be variously configured according to the requirements of a particular application. Portion 48 includes a mounting surface 59 that defines two spaced apart openings 60 and 62 that are configured for engagement with a first implant gripping portion 64, to fix portion 64 at end 36 of extender 32. In one embodiment, a part of a surface surrounding opening 58 extends distally above a portion of surface 59 and is configured to overlap a portion of portion 64 to facilitate fixation of portion 64 to portion 48.

Portion 64 and a second implant gripping portion are configured such that gripping portions are disposable between a first orientation, to load and/or eject a first implant and a second orientation, to engage and secure a first implant, as described herein. Portion 64 comprises a first jaw 66 and a second jaw 68. Jaw 66 extends between a first end 70 and a second end 72, and includes an outer surface 74. A projection 76 (FIG. 15) is defined from surface 74 and is disposed adjacent end 70. Projection 76 is disposed within opening 60. It is contemplated that projection 76 may alternatively be a hook, clip, rod, tab, detent and/or key/keyway. A portion of end 70 is angled and is configured for engagement with an end of a locking member. Surface 74 defines a cavity 78 (FIG. 15) that is configured for engagement with a component of a locking member, such as, for example, a biasing member.

Jaw 66 includes a capture member 80 disposed adjacent end 72. Member 80 includes an inner surface that defines an implant cavity configured for disposal of a portion of a first implant, such as, for example, a bone fastener 82. The inner surface of member 80 includes a fixation surface, such as, for example, a tab 84 that extends into the implant cavity of member 80 to engage bone fastener 82 for retaining bone fastener 82 in a selective orientation. The inner surface includes a planar face and an arcuate face. It is contemplated that all or only a portion of the inner surface may have alternate surface configurations to enhance fixation with bone fastener 82, such as, for example, dimpled and/or textured. It is contemplated that tab 84 may include a nail configuration, raised elements and/or spikes to facilitate engagement of the members with bone fastener 82.

Figure 6:
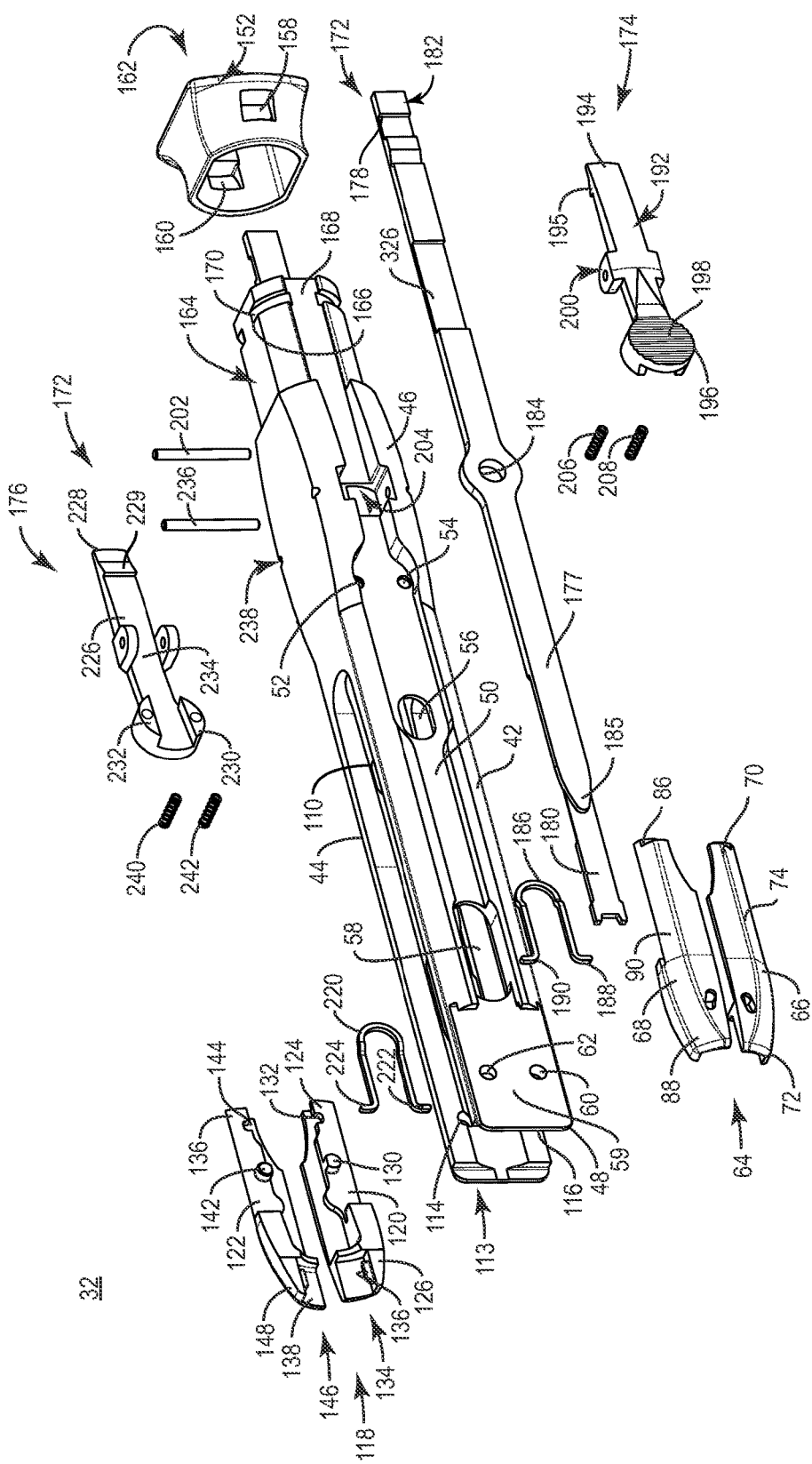
FIG. 6 is an exploded perspective view of components of the system shown in FIG. 1.
Figure 9:
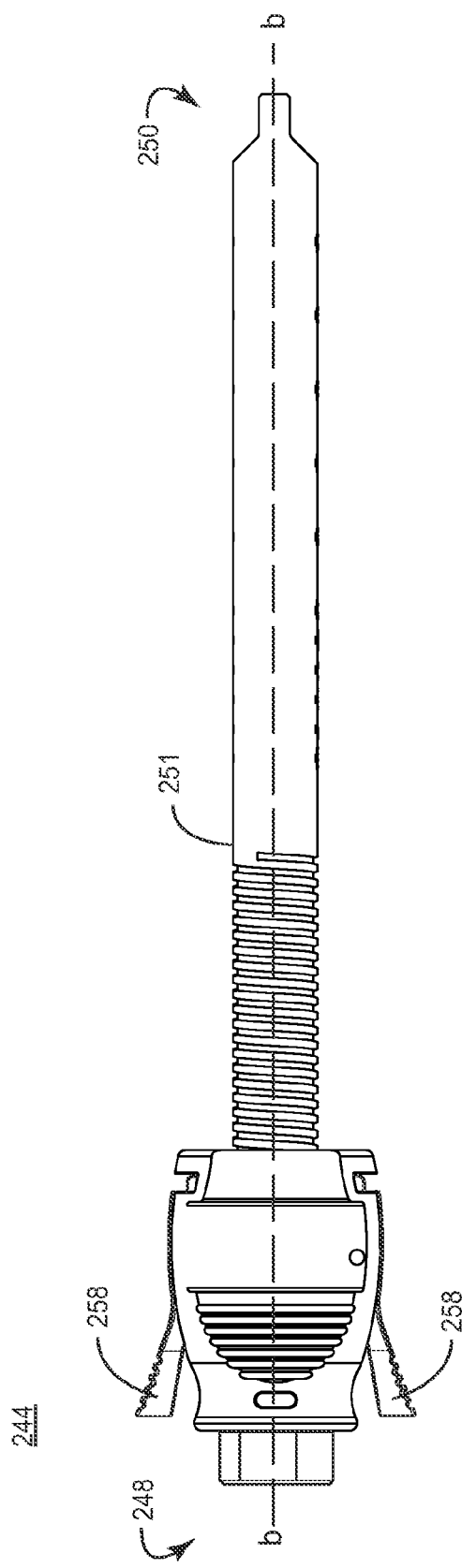
FIG. 9 is a side view of components of the system shown in FIG. 1.
Figure 10:
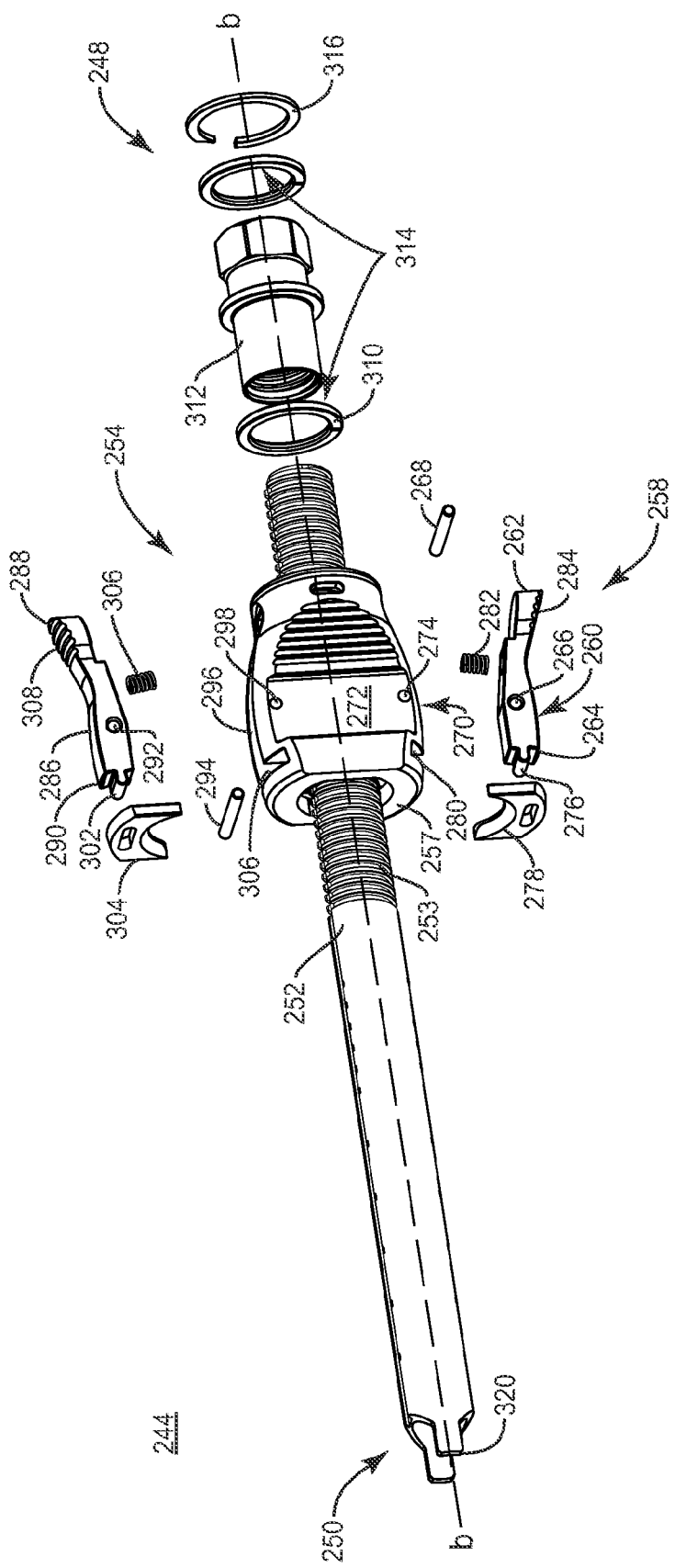
FIG. 10 is an exploded perspective view of the components shown in FIG. 9.
Figure 11:
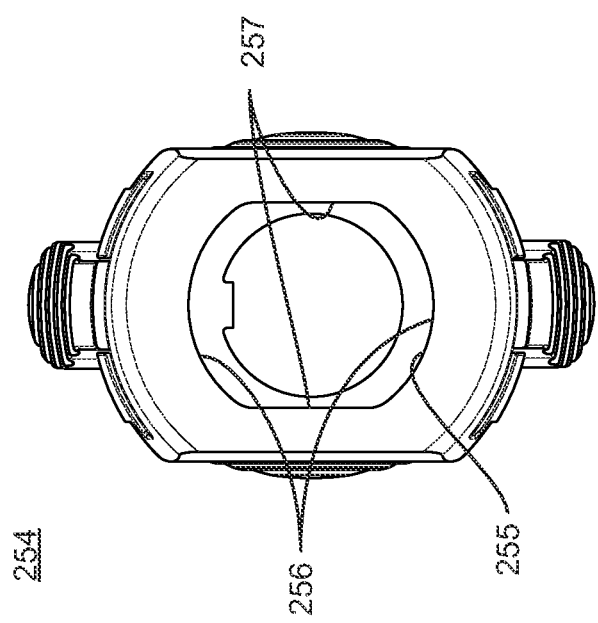
FIG. 11 is an enlarged top view of the components shown in FIG. 10.
Figures 12, 13:
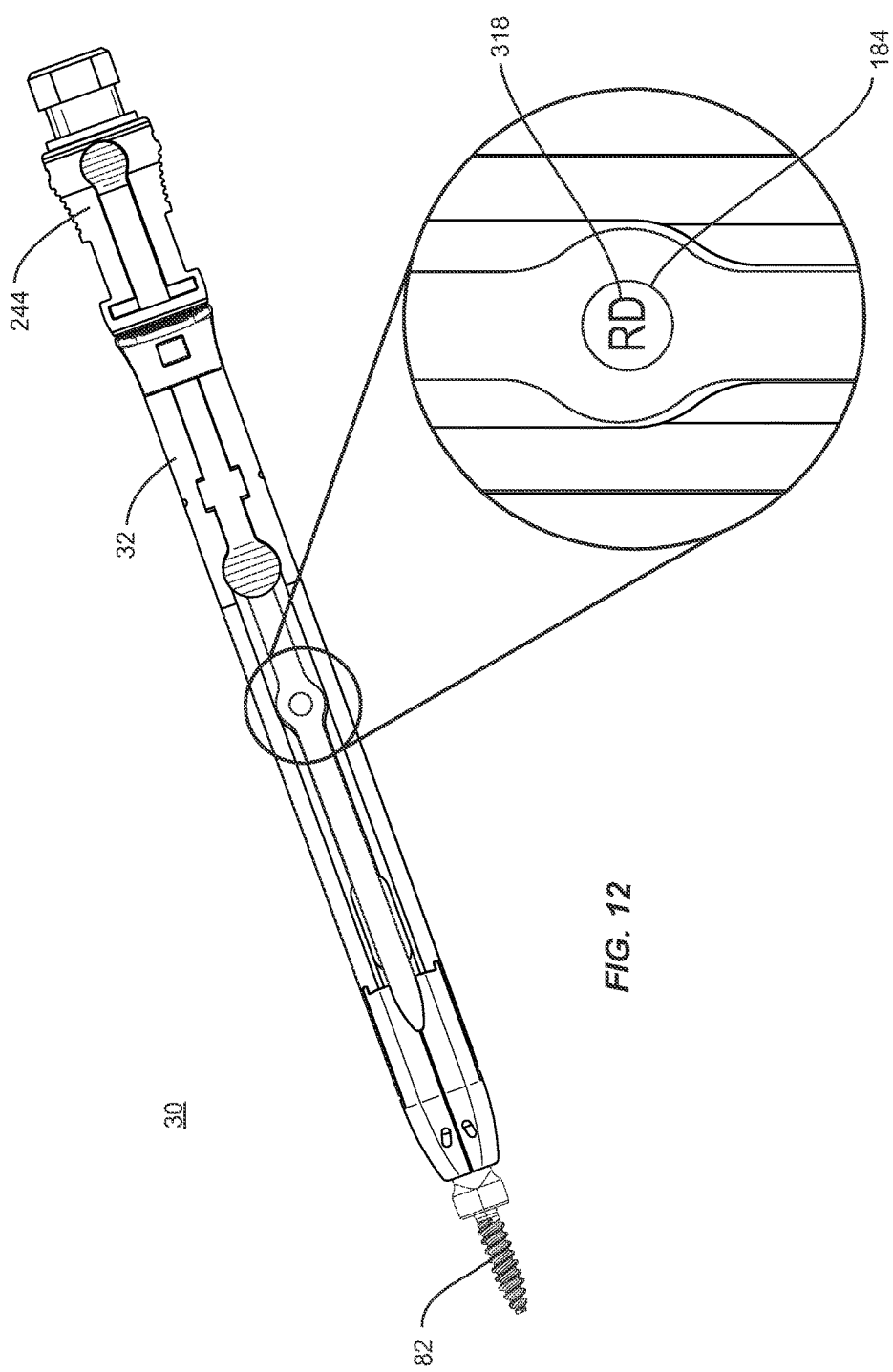
FIG. 12 is a perspective view of components of one embodiment of a system in accordance with the principles of the present disclosure.
FIG. 13 is an enlarged break away view of the components shown in FIG. 12.
Figure 15:
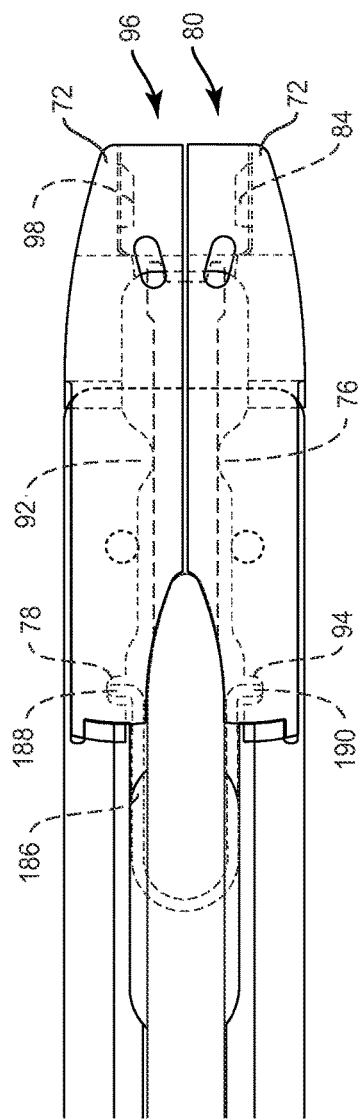
FIG. 15 is an enlarged break away view of the components shown in FIG. 14.

Jaw 68 extends between a first end 86 and a second end 88, and includes an outer surface 90 (FIG. 6). A projection 92 is defined from surface 90 and is disposed adjacent end 86 (FIG. 15). Projection 92 is disposed within opening 62. It is contemplated that projection 92 may alternatively be a hook, clip, rod, tab, detent and/or key/keyway. A portion of end 86 is angled and is configured for engagement with an end of a locking member. Surface 90 defines a cavity 94 configured for engagement with a component of a locking member, such as, for example, a biasing member.

Jaw 68 includes a capture member 96 disposed adjacent end 88. Member 96 includes an inner surface that defines an implant cavity configured for disposal of a portion of bone fastener 82. The inner surface of member 96 includes a fixation surface, such as, for example, a tab 98 that extends into the implant cavity of member 96 to engage bone fastener 82 for retaining bone fastener 82 in a selective orientation. The inner surface includes a planar face and an arcuate face. It is contemplated that all or only a portion of the inner surface may have alternate surface configurations to enhance fixation with bone fastener 82, such as, for example, dimpled and/or textured. It is contemplated that tab 98 may include a nail configuration, raised elements and/or spikes to facilitate engagement of the members with bone fastener 82.

Arm 44 extends between a proximal portion 100 and a distal portion 102. Arm 44 includes a wall that defines a channel 104 that extends between portions 100, 102. Channel 104 is configured for engagement with a portion of a locking member as described below. It is contemplated that channel 104 may have various configurations, such as, for example, cylindrical, partially cylindrical, rectangular, polygonal, irregular, tapered, offset, staggered, uniform and non-uniform.

Portion 100 includes two spaced apart openings 106, 108 configured for engagement with components of a locking member, such as, for example, biasing members. A window 110 is defined within channel 104 and is configured to align with a second window to indicate translation of a second instrument disposed within extender 32, as described herein. It is contemplated that window 110 may be variously configured such as, for example, round, cylindrical, partially cylindrical, oval, rectangular, polygonal, irregular, tapered, offset.

Portion 102 includes an opening 112 configured for disposal of components of a locking member, such as, for example, a biasing member. Opening 112 may be variously configured according to the requirements of a particular application. Portion 102 includes a mounting surface 113 that defines two spaced apart openings 114 and 116 that are configured for engagement with a second implant gripping portion 118, to fix portion 118 at end 36 of extender 32. In one embodiment, a part of a surface surrounding opening 112 extends distally above a portion of surface 113 and is configured to overlap a portion of portion 118 to facilitate fixation of portion 118 to portion 102.

Portion 118 and portion 64 are configured such that gripping portions are disposable between a first orientation, to load and/or eject bone fastener 82 and a second orientation, to engage and secure bone fastener 82, as described herein. Portion 118 comprises a first jaw 120 and a second jaw 122. Jaw 120 extends between a first end 124 and a second end 126, and includes an outer surface 128. A projection 130 is defined from surface 128 and is disposed adjacent end 124. Projection 130 is disposed within opening 116 of portion 102. It is contemplated that projection 130 may alternatively be a hook, clip, rod, tab, detent and/or key/keyway. A portion of end 124 is angled and is configured for engagement with an end of a locking member. Surface 128 defines a cavity 132 that is configured for engagement with a component of a locking member, such as, for example, a biasing member.

Jaw 120 includes a capture member 134 disposed adjacent end 126. Member 134 includes an inner surface that defines an implant cavity configured for disposal of a portion of bone fastener 82. The inner surface of member 134 includes a fixation surface, such as, for example, a tab 136 that extends into the implant cavity of member 134 to engage bone fastener 82 for retaining bone fastener 82 in a selective orientation. The inner surface includes a planar face and an arcuate face. It is contemplated that all or only a portion of the inner surface may have alternate surface configurations to enhance fixation with bone fastener 82, such as, for example, dimpled and/or textured. It is contemplated that tab 136 may include a nail configuration, raised elements and/or spikes to facilitate engagement of the members with bone fastener 82.

Jaw 122 extends between a first end 136 and a second end 138, and includes an outer surface 140. A projection 142 is defined from surface 140 and is disposed adjacent end 136. Projection 142 is disposed within opening 114 of portion 102. It is contemplated that projection 142 may alternatively be a hook, clip, rod, tab, detent and/or key/keyway. A portion of end 136 is angled and is configured for engagement with an end of a locking member. Surface 140 defines a cavity 144 that is configured for engagement with a component of a locking member, such as, for example, a biasing member.

Jaw 122 includes a capture member 146 disposed adjacent end 138. Member 146 includes an inner surface that defines an implant cavity configured for disposal of a portion of bone fastener 82. The inner surface of member 146 includes a fixation surface, such as, for example, a tab 148 that extends into the implant cavity of member 146 to engage bone fastener 82 for retaining bone fastener 82 in a selective orientation. The inner surface includes a planar face and an arcuate face. It is contemplated that all or only a portion of the inner surface may have alternate surface configurations to enhance fixation with bone fastener 82, such as, for example, dimpled and/or textured. It is contemplated that tab 148 may include a nail configuration, raised elements and/or spikes to facilitate engagement of the members with bone fastener 82.

End 34 of extender 32 includes a transverse wall 150. Wall 150 is configured for engagement with a locking member and a second instrument, as described herein. Wall 150 defines a cap 152. Cap 152 defines an axial wall 151 that is continuous and non-interrupted. Wall 151 has a tubular cross section configuration. Cap 152 includes a frictional surface, such as, for example, a first surface 154 and second surface 156. Surface 154 is spaced apart from surface 156 and both surfaces 154, 156 are grooved. It is contemplated that surfaces 154, 156 may have alternate surface configurations according to the requirements of a particular application. A first opening 158 and a second opening 160 are disposed adjacent surfaces 154, 156 respectively. Surfaces of openings 158, 160 are configured for engagement with a recess 162. Recess 162 is configured for engagement with a post 164 disposed at end 34.

Post 164 has a barrel cross-section configuration. Post 164 is configured for engagement with an inner surface of a second instrument, as described herein. Post 164 includes an outer surface that defines arcuate surfaces, such as, for example, transverse ribs 166. Ribs 166 engage with an inner surface of a second instrument that defines an arcuate section and a linear section, as described below. It is contemplated that post 164 can include one or a plurality of arcuate sections. Post 164 includes linear surfaces, such as, for example, channel surfaces 168 and side walls 170 that are configured for engagement with a locking member 172. It is contemplated that post 164 can include one or a plurality of linear surfaces.

Member 172 is configured to selectively lock extender 32 in an expanded or non expanded orientation and prevents undesired disengagement of bone fastener 82 from portions 64, 118. It is contemplated that undesirable disengagement can include accidental, inadvertent and/or component failure. Member 172 includes a first lock 174 and a second lock 176. Locks 174, 176 are independently actuated for simultaneously capturing and/or releasing bone fastener 82 such that actuation of only one lock will not disengage bone fastener 82.

Lock 174 includes a first shaft 177 configured for disposal within channel 50 of arm 42 and engagement with cap 152. Shaft 177 extends between a first end 178 and a second end 180. End 178 includes a flange 182 configured for disposal with opening 158 of cap 152. An opening 184 is disposed between ends 178, 180. Opening 184 is configured to align with window 56 and visual indicia disposed on a second instrument that translates within and relative to extender 32, indicating advancement of the second instrument through extender 32 to a selected distance relative to extender 32. End 180 defines a tapered portion 185 and a bifurcated section configured for engagement with a biasing member 186 disposed within opening 58. Biasing member 186 includes a first member 188 and a second member 190 configured for engagement with cavities 78, 94 of jaws 66, 68 respectively.

Lock 174 includes a latch 192 that extends between a first portion 194 and a section portion 196. Portion 194 includes a lip 195 configured for engagement with shaft 177. Portion 196 includes a depressible member, such as, for example, a button 198. A transverse channel 200 is located adjacent button 198 and is configured for engagement with a pin 202 to connect latch 192 within a recess 204 defined within arm 42. Biasing members, such as, for example, springs 206, 208 are disposed within openings 52, 54 and engage an underside of button 198.

Lock 176 includes a second shaft 210 configured for disposal within channel 104 of arm 44 and engagement with cap 152. Shaft 210 extends between a first end 212 and a second end 214. End 212 includes a flange 216 configured for engagement with opening 160 of cap 152. An opening 218 is disposed between ends 212, 214. Opening 218 is configured to align with window 110 and visual indicia disposed on a second instrument that translates within extender 32, indicating advancement of the second instrument through extender 32 to a selected distance relative to extender 32. End 214 defines a tapered portion 219 and a bifurcated section configured for engagement with a biasing member 220 disposed within opening 112. Biasing member 220 includes a first member 222 and a second member 224 configured for engagement with cavities 132, 144 of jaws 120, 122 respectively.

Lock 176 includes a latch 226 that extends between a first portion 228 and a section portion 230. Portion 228 includes a lip 229 configured for engagement with shaft 210. Portion 230 includes a depressible member, such as, for example, a button 232. A transverse channel 234 is located adjacent button 232 and is configured for engagement with a pin 236 to connect latch 226 within a recess 238 defined within arm 44. Biasing members, such as, for example, springs 240, 242 are disposed within openings 106, 108 and engage an underside of button 232.

Spinal implant system 30 includes a second instrument, such as, for example, a reducer 244. Reducer 244 is configured for engagement and disposal within passageway 37 of extender 32 such that reducer 244 and extender 32 facilitate disposal of bone fastener 82 at a surgical site and reduction of a second implant, such as, for example, a rod 246 within a top portion of bone fastener 82. Reducer 244 extends between a first end 248 and a second end 250. Reducer 244 defines a second longitudinal axis b. It is contemplated that the cross-section of reducer 244 may have various configurations, for example, round, cylindrical, partially cylindrical, oval, rectangular, polygonal, irregular, tapered, offset, staggered, uniform and non-uniform. It is further envisioned that one or all of the surfaces of reducer 244 may have alternate surface configurations, such as, for example, rough, threaded for connection with surgical instruments, arcuate, undulating, porous, semi-porous, dimpled, polished and/or textured according to the requirements of a particular application.

Reducer 244 includes an outer surface 252 that defines an elongated shaft 251. Shaft 251 defines a threaded portion 253 disposed adjacent end 248. Portion 252 is configured for engagement with a reduction housing 254. Housing 254 includes a continuous inner surface 255 that comprises a barrel cross section barrel configuration and is recessed within housing 254. Surface 255 comprises arcuate surfaces, such as, for example, arcuate walls 256. Walls 256 are configured for mating engagement with ribs 166 disposed on post 164 of extender 32 such that extender 32 is seated and/or nested in a selected relative orientation of ends 34, 248 of extender 32 and reducer 244 respectively. It is contemplated that surface 255 can include one or a plurality of arcuate sections. Surface 255 includes linear walls 257 configured for mating engagement with extender 32. It is contemplated that surface 255 can include one or a plurality of linear surfaces such that extender 32 is seated and/or nested in a selected relative orientation of ends 34, 248 of extender 32 and reducer 244 respectively. The mating engagement configuration of ribs 166, walls 256 and surfaces 168/side walls 170 and walls 257, facilitates alignment of extender 32 with reducer 244, for example 0, 180 and 360 degree relative angular orientation, for assembly of the components and avoids undesired assembly of the components when extender 32 and reducer 244 are misaligned, for example 90 degree relative angular orientation.

Housing 254 includes a lock 258. Lock 258 comprises a first latch release 260 that extends between a proximal end 262 and a distal end 264. Release 260 includes an opening 266. A pin 268 connects release 260 within a cavity 270 defined within a side portion of housing 254. Pin 268 is disposed within an opening 274 defined by an outer surface 272 of housing 254 and inserts into opening 266. End 264 includes a prong 276 that engages with a latch 278 disposed within a recess 280 of housing 254. End 262 engages with a biasing member, such as, for example, a spring 282. A button 284 is positioned on end 262. Button 284 is depressible and engages with spring 282 causing prong 276 to engage with latch 278 to lock reducer 244 with extender 32, as described herein. Lock 258 comprises a second latch release 286 that extends between a proximal end 288 and a distal end 290. Release 286 includes an opening 292. A pin 294 connects release 286 within a cavity 296 defined within a side portion of housing 254. Pin 294 is disposed into an opening 298 defined by surface 272 of housing 254 and inserts into opening 292. End 290 includes a prong 302 that engages with a latch 304 disposed within a recess 306 of housing 254. End 288 engages with a biasing member, such as, for example, a spring 306. A button 308 is positioned on end 288. Button 308 is depressible and engages with spring 306 causing prong 302 to engage with latch 286 to lock reducer 244 with extender 32, as described herein.

A first bearing 310, a reduction nut 312, a second bearing 314 and a retaining ring 316 are disposed on end 248 and are configured for engagement with portion 252 and housing 254 as housing 254 is translated via portion 253. Surface 252 includes visual indicia 318 disposed between portion 253 and end 250. Indicia 318 is configured to display the axial translation of reducer 244 within extender 32 via windows 56, 184 and 110, 218. In one embodiment, upon selective axial translation of reducer 244 relative to extender 32 to reduce a spinal rod with a head of a bone fastener, the visual indicia, for example, marking RD is displayed through windows 56, 184 to indicate that the spinal rod is reduced with the bone fastener. In one embodiment, the visual indicia can include graduations and/or numerical markers to indicate depth of penetration of the spinal rod with the bone fastener and/or depth of an implant at a surgical site.

End 250 includes an implant engaging portion 320. Portion 320 is pronged and is configured for engagement with rod 246. It is contemplated that portion 320 may have alternate configurations, such as, for example, a hook, clip, tab and/or a detent. Portion 320 is translatable relative to end 248 to reduce rod 246 within bone fastener 82 as the reduction nut 312 is rotated.

Figure 14:
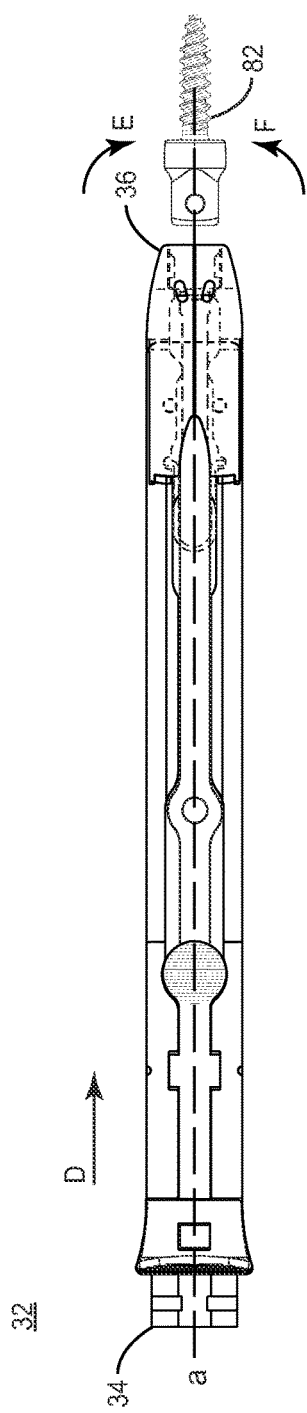
FIG. 14 is a side view of components of the system shown in FIG. 1.

In operation, the surfaces of jaws 66, 68 of portion 64 of arm 42 and jaws 120, 122 of portion 118 of arm 44 are disposed in a flush contacting engagement in the non expanded orientation and bone fastener 82 is disposed adjacent end 36, as shown in FIG. 14. Flanges 182, 216 of shafts 177, 210 are disposed with openings 158, 160 of cap 152 respectively. Jaws 66, 68 and jaws 120, 122 also cooperate to define channels 322, 324 which receive shafts 177, 210. Shafts 177, 210 are positioned in engagement with jaws 66, 68 and jaws 120, 122. More particularly, as shafts 177, 210 are moved distally within channels 50, 104, portions 185, 219 of shafts 177, 210 are positioned in a recess between jaws 66, 68 and 120, 122 and engage with correspondingly shaped surfaces on jaws 66, 68 and 120, 122 until portions 185, 219 are positioned against jaws 66, 68 and 120, 122. As shafts 177, 210 are moved in this manner, portions 185, 219 apply an additional spreading force to ends 72, 88 and 126, 138, which in turn also forces ends 72, 88 and 126, 138 toward each other.

Portions 185, 219 are positioned against jaws 66, 68 and jaws 120, 122 to prevent movement of ends 72, 88 and 126, 138 toward each other such that ends 72, 88 and 126, 138 cannot be moved away from each other. Lips 195, 229 of latches 192, 226 engage with shafts 177, 210 respectively. Ends 180, 214 of shafts 177, 210 are disposed adjacent biasing members 186, 220. Biasing members 186, 220 engage with openings 58, 112 and members 188, 190 and 224, 224 are disposed with cavities 78, 94 and 132, 144 respectively.

To attach bone fastener 82 to extender 32 and dispose portions 64, 118 in the expanded orientation, buttons 198 and 232 are depressed, causing lips 195, 229 to disengage from shafts 177, 210. Cap 152 is axially translated in a direction, such as, for example, a proximal direction, as shown by arrow A in FIG. 16. Shafts 177, 210 are axially translated in the direction of arrow A via cap 152. Portions 185, 219 disengage from channels 322, 324 and ends 180, 214 of shafts 177, 210 disengage from biasing members 186, 220. Portions 64, 118 pivotably expand and separate in a direction, such as, for example, an outward direction, as shown by arrows B and C. Locking slots defined on a proximal end of bone fastener 82 engage with tabs 84, 98 and 136, 148 of members 80, 96 and 134, 146 respectively.

To place extender 32 in the non expanded locked orientation, cap 152 is axially translated in a direction, such as, for example, a distal direction, as shown by arrow D in FIG. 14. Shafts 177, 210 are translated in the direction of arrow D via cap 152. Portions 185, 219 engage with channels 322, 324 and ends 180, 214 of shafts 177, 210 engage with biasing members 186, 220. Ends 180, 214 engage biasing members 186, 220 to retract jaws 66, 68 and 120, 122. Portions 64, 118 retract in a direction, such as, for example, an inward direction, as shown by arrows E and F. Portions 64, 118 are placed in a flushed engagement, locking bone fastener 82 with extender 32 via tabs 84, 98 and 136, 148. Buttons 198 and 232 are lifted to facilitate engagement of lips 195, 229 with grooves 326, 328 on shafts 177, 210.

To dispose rod 246 with bone fastener 82, reducer 244 is connected to extender 32 via end 34 and housing 254, and shaft 251 is inserted into passageway 37. The mating surfaces of extender 32 and reducer 244 are manipulated for mating engagement such that extender 32 is seated and/or nested in a selected relative orientation of ends 34, 248 of extender 32 and reducer 244 respectively, as described above. Ribs 166 and surfaces 168/side walls 170 are rotated in a clockwise direction, as shown by arrow G in FIG. 1, for example 180 degrees, relative to walls 256, 257 to align the mating surfaces of extender 32 with the mating surfaces of reducer 244 for assembly of the components of system 30.

Reducer 244 is locked to extender 32 via latch releases 260, 286 of lock 258. Button 284 is depressed and engages spring 282 causing prong 276 to engage latch 278. Latch 278 is placed in a downward direction, locking with post 164. Button 308 is depressed and engages with spring 306 causing prong 302 to engage with latch 286. Latch 286 is placed in a downward direction, locking post 164. To unlock reducer 244 from extender 32, buttons 284 and 308 are depressed, causing latches 278, 286 to disengage from post 164.

Figure 18:
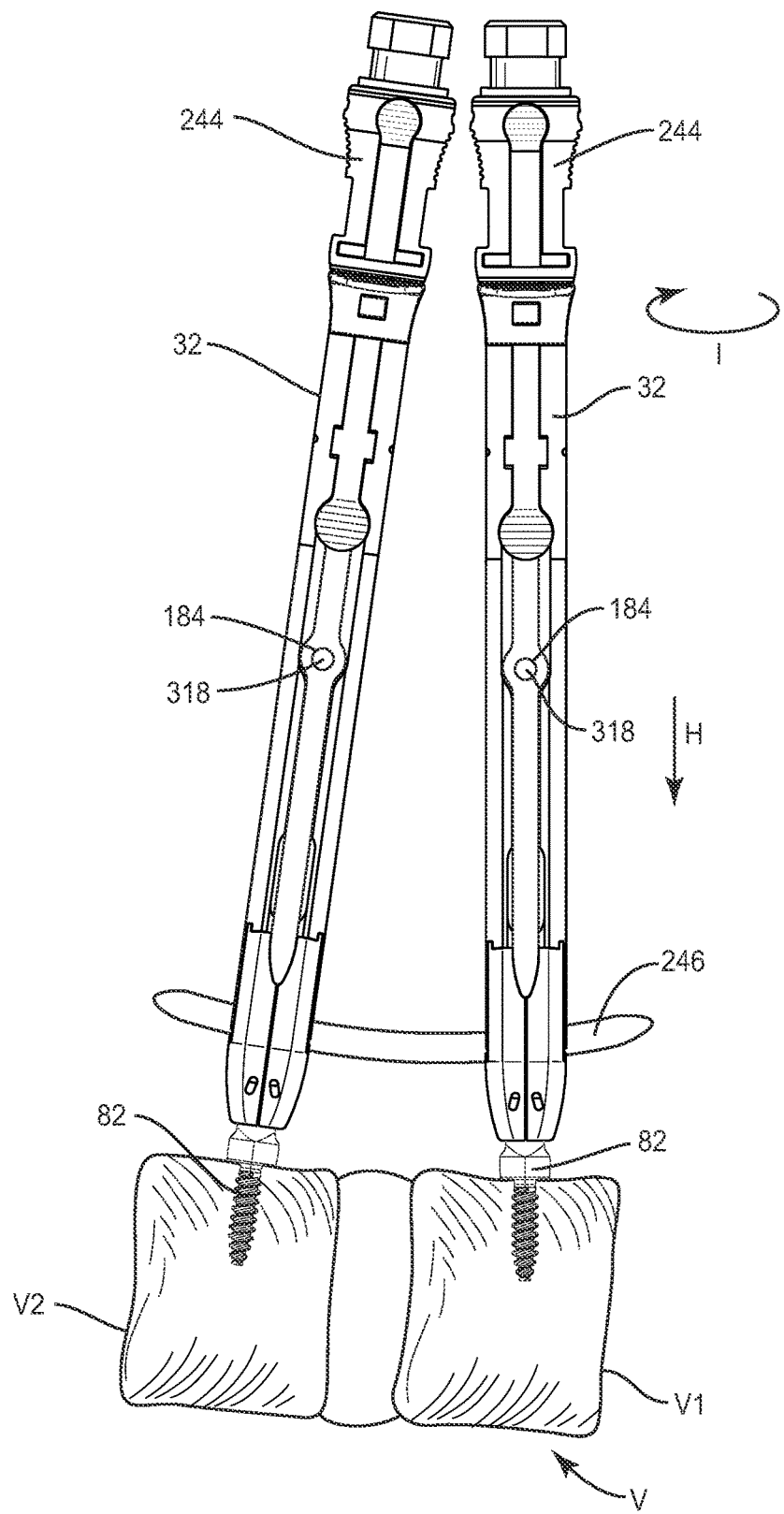
FIG. 18 is a plan view of one embodiment of a system in accordance with the principles of the present disclosure disposed with vertebrae.
Figure 19:
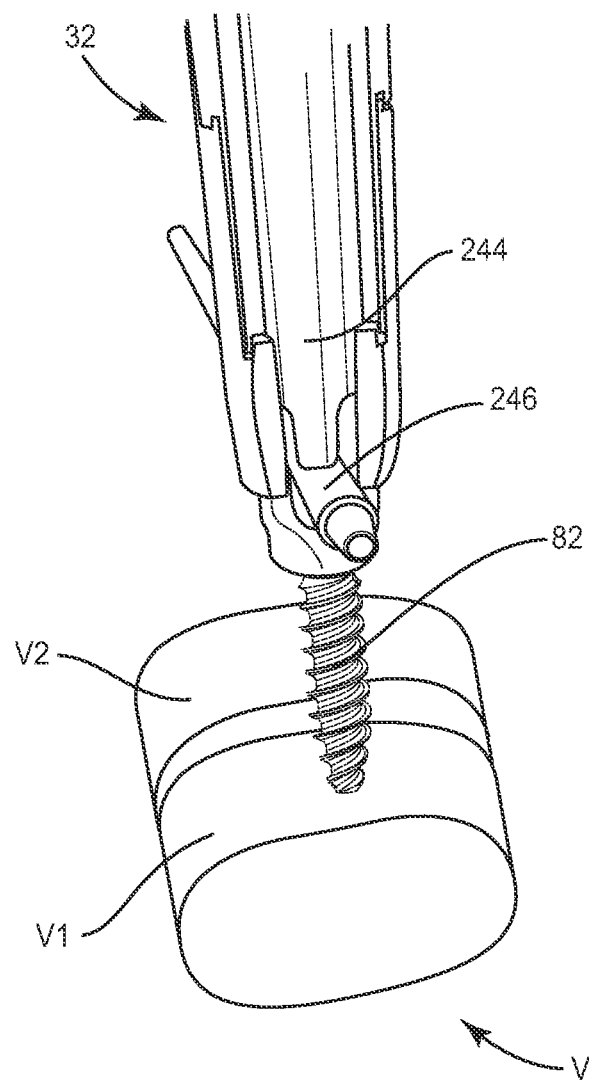
FIG. 19 is a break away view of the components and vertebrae shown in FIG. 18.
Figure 20:
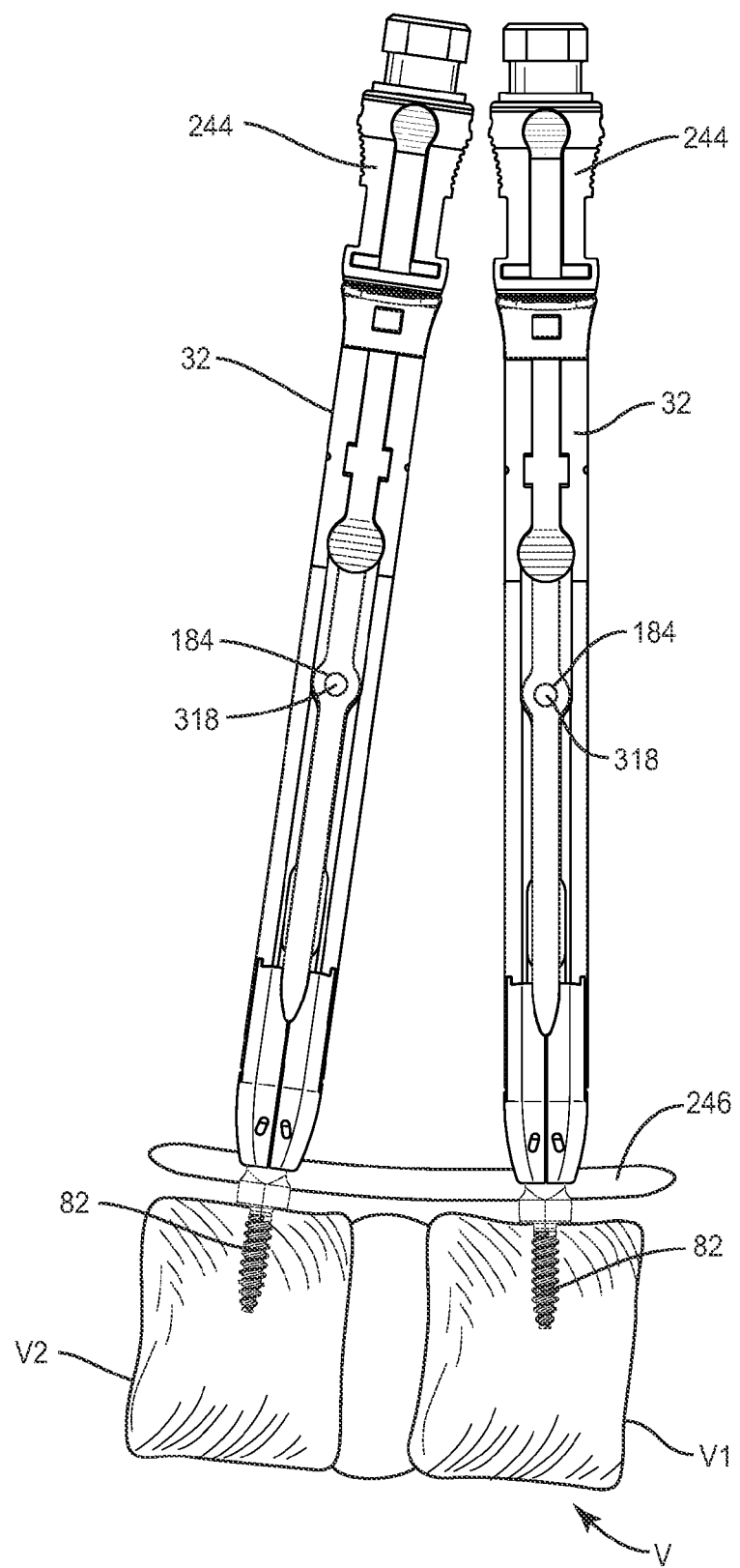
FIG. 20 is a plan view of the components and vertebrae shown in FIG. 18.

In assembly, operation and use, spinal implant system 30 is employed with a surgical procedure for treatment of a spinal disorder affecting a section of a spine of a patient, as discussed herein. Spinal implant system 30 may also be employed with other surgical procedures. For example, spinal implant system 30 can be used with a surgical procedure for treatment of a condition or injury of an affected section of the spine including vertebrae V, as shown in FIGS. 18-20.

In use, to treat the affected section of vertebrae V, a medical practitioner obtains access to a surgical site including vertebrae V1, V2 in any appropriate manner, such as through incision and retraction of tissues. It is envisioned that spinal implant system 30 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. Spinal implant system 30 is then employed to augment the surgical treatment. Spinal implant system 30 can be delivered or implanted as a pre-assembled device or can be assembled in situ. Spinal implant system 30 may be completely or partially revised, removed or replaced during or after the surgical procedure.

An incision is made in the body of a patient and a cutting instrument (not shown) creates a surgical pathway for implantation of components of spinal implant system 30. A preparation instrument (not shown) can be employed to prepare tissue surfaces of vertebrae V, as well as for aspiration and irrigation of a surgical region according to the requirements of a particular surgical application. Pilot holes or the like are made in vertebrae V1, V2 for receiving the shaft of bone fastener 82. Spinal implant system 30 is disposed adjacent vertebrae V at a surgical site.

To attach bone fastener 82 to extender 32 and dispose portions 64, 118 in the expanded orientation, buttons 198 and 232 are depressed, causing lips 195, 229 to disengage from shafts 177, 210. Cap 152 is axially translated in a proximal direction, as shown by arrow A. Shafts 177, 210 are axially translated in the direction of arrow A via cap 152. Portions 185, 219 disengage from channels 322, 324 and ends 180, 214 of shafts 177, 210 disengage from biasing members 186, 220. Portions 64, 118 pivotably expand and separate in an outward direction, as shown by arrows B and C. Locking slots defined on a proximal end of bone fastener 82 engage with tabs 84, 98 and 136, 148 of members 80, 96 and 134, 146 respectively.

To place extender 32 in the non expanded locked orientation, cap 152 is axially translated in a distal direction, as shown by arrow D in FIG. 14. Shafts 177, 210 are translated in the direction of arrow D via cap 152. Portions 185, 219 engage channels 322, 324 and ends 180, 214 of shafts 177, 210 engage with biasing members 186, 220. Ends 180, 214 engage biasing members 186, 220 to retract jaws 66, 68 and 120, 122. Portions 64, 118 retract in an inward direction, as shown by arrows E and F. Portions 64, 118 are placed in flush engagement, locking bone fastener 82 with extender 32 via tabs 84, 98 and 136, 148. Buttons 198 and 232 are lifted to facilitate engagement of lips 195, 229 with grooves 326, 328 on shafts 177, 210.

To dispose rod 246 with bone fastener 82, reducer 244 is connected to extender 32 via end 34 and housing 254, and shaft 251 is inserted into passageway 37. The mating surfaces of extender 32 and reducer 244 are manipulated for mating engagement such that extender 32 is seated and/or nested in a selected relative orientation of ends 34, 248 of extender 32 and reducer 244 respectively, as described above.

Reducer 244 is locked to extender 32 via latch releases 260, 286 of lock 258. Button 284 is depressed and engages with spring 282 causing prong 276 to engage with latch 278. Latch 278 is placed in a downward direction, locking with post 164. Button 308 is depressed and engages with spring 306 causing prong 302 to engage with latch 286. Latch 286 is placed in a downward direction, locking with post 164. To unlock reducer 244 from extender 32, buttons 284 and 308 are depressed, causing latches 278, 286 to disengage from post 164.

Rod 246 is inserted transversely into passageway 37 adjacent end 34. Shaft 251 is axially translated in a distal direction, shown by arrow H in FIG. 18 within passageway 37 via portion 253 rotating in a clockwise direction, shown by arrow I, within housing 254. Indicia 318, as described above with regard to FIGS. 12-13, are viewed via windows 56, 110 and openings 184, 218 of extender 32 while engaging portion 320 of reducer 244 engages a surface of rod 246 to reduce rod 246 within a top portion of bone fastener 82, as shown in FIGS. 19-20.

Upon completion of the procedure, the non-implanted components of system 30, surgical instruments and assemblies are removed and the incision is closed. Spinal implant system 30 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of spinal implant system 30.

It is contemplated one or a plurality of bone fasteners may be employed with a single vertebral level. It is further contemplated that the bone fasteners may be engaged with vertebrae in various orientations, such as, for example, series, parallel, offset, staggered and/or alternate vertebral levels. It is envisioned that the bone fasteners may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. These bone fasteners may be coated with an osteoinductive or osteoconductive material to enhance fixation, and/or include one or a plurality of therapeutic agents.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
  a first instrument comprising a body extending between a first end including an outer surface and a second end comprising spaced apart arms, the first instrument comprising gripping portions coupled to the arms and configured for engaging a first implant, the body defining a passageway, the body comprising opposite first and second grooves, the first instrument comprising a cap that is removably coupled to the body and strips disposed in each of the grooves, the strips being coupled to the cap, the cap comprising flanges disposed in each of the grooves; and
  a second instrument comprising a first end including a housing having an inner surface defining an opening, the second instrument comprising a monolithic shaft having a threaded first end and a second end configured for engaging a second implant, the shaft being configured for disposal within the passageway, the body being positioned within the opening such that a linear surface of the inner surface engages a linear surface of the outer surface to prevent the body from rotating relative to the housing,
  wherein the gripping portions are pivotable relative to the arms such that the gripping portions are disposable between an expanded orientation and a non expanded orientation to engage the first implant and the shaft is axially translatable relative to the housing to dispose the second implant with the first implant, the cap being configured to translate axially relative to the body to move the gripping portions between the expanded and non-expanded orientations, and wherein the first instrument includes a window that extends through one of the grooves and a window that extends through one of the strips, the second instrument including visual indicia that aligns with the windows to indicate a position of the second implant relative to the first implant.

2. A system as recited in claim 1, wherein the first end of the body includes a wall having the outer surface, the wall being continuous and non-interrupted.

3. A system as recited in claim 1, wherein the first end of the body includes an axial wall having a tubular configuration and a transverse wall.

4. A system as recited in claim 3, wherein the transverse wall includes at least one frictional surface.

5. A system as recited in claim 3, wherein the transverse wall includes a first frictional surface and a second frictional surface spaced apart from the first frictional surface.

6. A system as recited in claim 1, wherein the inner surface is continuous and includes facing linear surfaces and facing arcuate surfaces that define a recess such that the outer surface is seated therein.

7. A system as recited in claim 1, wherein the linear surface of the inner surface includes opposite first and second linear surfaces, the inner surface comprising opposite first and second arcuate surfaces between the first and second linear surfaces, the linear surface of the outer surface including opposite third and fourth linear surfaces, the outer surface comprising opposite third and fourth arcuate surfaces between the third and fourth linear surfaces, the first and second linear surfaces engage the third and fourth linear surfaces and the first and second arcuate surfaces engage the third and fourth arcuate surfaces to align the first instrument with the second instrument.

8. A system as recited in claim 1, wherein the inner surface is configured for alignment with the outer surface such the first end of the body is disposed in a nested configuration with the first end of the second instrument.

9. A system as recited in claim 1, wherein the opening has a barrel configuration and the outer surface includes a post having a barrel configuration, the post comprising the linear surface of the outer surface, the inner surface being configured for alignment with the outer surface such that the first end of the body is seated with the first end of the second instrument.

10. A system as recited in claim 1, wherein the first instrument includes a first lock and a second lock, the locks each being configured to releasably engage one of the strips, the locks being independently actuated for capturing the first implant.

11. A system as recited in claim 10, wherein the locks are configured for simultaneous engagement to release the first implant.

12. A system as recited in claim 1, further comprising the first implant, wherein the gripping portions each comprise a pair of tabs and the first implant comprises two pairs of locking slots, the tabs being spaced apart from the locking slots when the first instrument is in the expanded orientation, the tabs being disposed within the locking slots when the first instrument is in the non-expanded orientation.

13. A system as recited in claim 1, wherein the cap is configured to translate axially relative to the body to move the strips such that distal ends of the strips engage biasing members of the first instrument such that the biasing members cause the gripping portions to retract inwardly to move the first instrument from the expanded orientation to the non-expanded orientation.

14. A system as recited in claim 1, wherein the cap is configured to translate axially relative to the body to move the strips such that distal ends of the strips disengage biasing members of the first instrument such that the biasing members cause the gripping portions deflect outwardly to move the first instrument from the non-expanded orientation to the expanded orientation.

15. A system as recited in claim 1, wherein the inner surfaces is unthreaded and the shaft comprises a threaded outer surface that engages the inner surface, the second instrument comprising a reduction nut configured to engage the housing, the reduction nut having a threaded inner surface that engages the threaded outer surface such that rotation of the reduction nut causes the housing to translate axially relative to the shaft.

16. A system as recited in claim 1, wherein the arms comprise a first arm and a second arm and the gripping portion comprises a first gripping portion coupled to the first arm and a second gripping portion coupled to the second arm, the first and second gripping portions each including first and second jaws that move relative to one another as the gripping portions move between the expanded and non expanded orientations.

17. A spinal implant system comprising:
an extender comprising a body extending between a first end including an outer surface having a linear surface and an arcuate surface, and a second end comprising spaced apart arms, the extender comprising gripping portions coupled to the arms and configured for engaging a first implant, the extender defining a passageway, the body comprising opposite first and second grooves, the extender comprising a cap that is removably coupled to the body and strips disposed in each of the grooves, the strips being coupled to the cap, the cap comprising flanges disposed in each of the grooves; and
a reducer comprising a first end including a housing having an inner surface defining an opening, the inner surface comprising a linear surface and an arcuate surface, the second instrument comprising a monolithic shaft having a threaded first end and a second end configured for engaging a second implant, the shaft being configured for disposal within the passageway, the body being inserted into the opening such that the linear surfaces engage one another and the arcuate surfaces to prevent the body from rotating relative to the housing,
wherein the gripping portions are pivotable relative to the arms such that the gripping portions are disposable between an expanded orientation and a non expanded orientation to engage the first implant and the shaft is axially translatable relative to the housing to dispose the second implant with the first implant, the cap being configured to translate axially relative to the body to move the gripping portions between the expanded and non-expanded orientations, and
wherein the extender includes a window that extends through one of the grooves and a window that extends through one of the strips, the reducer including visual indicia that aligns with the windows to indicate a position of the second implant relative to the first implant.

18. A spinal implant system comprising:

an extender comprising a body extending between a first end including an outer surface having a linear surface and an arcuate surface and a second end comprising spaced apart arms, the extender comprising gripping portions coupled to the arms, the extender defining a passageway, the body comprising opposite first and second grooves, the extender comprising a cap that is removably coupled to the body and strips disposed in each of the grooves, the strips being coupled to the cap, the cap comprising flanges disposed in each of the grooves;

a reducer comprising a first end including a housing having an inner surface defining an opening, the inner surface comprising a linear surface and an arcuate surface, the second instrument comprising a monolithic shaft having a threaded first end and a second end comprising spaced apart prongs configured for engaging a spinal rod, the shaft being configured for disposal within the passageway, the body extending through the opening such that the linear surfaces engage one another and the arcuate surfaces engage one another to prevent the body from rotating relative to the housing;

a bone fastener defining an implant cavity, the gripping portions being configured to engage the bone fastener; and the spinal rod, wherein the gripping portions are pivotable relative to the arms such that the gripping portions are disposable between an expanded orientation and a non expanded orientation to engage the bone fastener and the shaft is translatable relative to the housing to dispose the spinal rod with the implant cavity, the cap being configured to translate axially relative to the body to move the gripping portions between the expanded and non-expanded orientations, and wherein the extender includes a window that extends through one of the grooves and a window that extends through one of the strips, the reducer including visual indicia that aligns with the windows to indicate a position of the second implant relative to the first implant.

* * * * *

UNITED STATES PATENT AND TRADEMARK OFFICE
CERTIFICATE OF CORRECTION

PATENT NO. : 9,918,752 B2
APPLICATION NO. : 13/689312
DATED : March 20, 2018
INVENTOR(S) : Hennard et al.

Page 1 of 1

It is certified that error appears in the above-identified patent and that said Letters Patent is hereby corrected as shown below:

In the Specification

In Column 10, Line 35, delete "Portion 252" and insert -- Portion 253 --, therefor.

In Column 11, Line 21, delete "portion 252" and insert -- portion 253 --, therefor.

In Column 11, Line 30, delete "windows 56, 184" and insert -- windows 56, 110 --, therefor.

Signed and Sealed this
Thirty-first Day of July, 2018

Andrei Iancu
*Director of the United States Patent and Trademark Office*